(12) United States Patent
Fein et al.

(10) Patent No.: US 6,813,008 B2
(45) Date of Patent: *Nov. 2, 2004

(54) MICRODISSECTION OPTICAL SYSTEM

(75) Inventors: Howard Fein, Richmond Heights, OH (US); Andrew G. Cartlidge, Palm Beach Gardens, FL (US)

(73) Assignees: Palantyr Research, LLC, Cleveland, OH (US); Angkor Technology, LLP, Cleveland, OH (US); Himanshu S. Amin, Twinsburg, OH (US); Daniel B. Bortnick, Mentor, OH (US); Gregory Turocy, Westlake, OH (US)

( * ) Notice: Subject to any disclaimer, the term of this patent is extended or adjusted under 35 U.S.C. 154(b) by 90 days.

This patent is subject to a terminal disclaimer.

(21) Appl. No.: 10/165,929

(22) Filed: Jun. 10, 2002

(65) Prior Publication Data

US 2003/0227611 A1 Dec. 11, 2003

(51) Int. Cl.[7] .............................................. G01N 1/00
(52) U.S. Cl. ...................................................... 356/36
(58) Field of Search ........................... 356/36, 73, 72, 356/326–327; 250/216, 208.1, 201.5, 227.26; 382/295

(56) References Cited

U.S. PATENT DOCUMENTS

| | | | |
|---|---|---|---|
| 4,750,022 A | | 6/1988 | Araki .......................... 355/46 |
| 5,051,770 A | | 9/1991 | Cornuejols .................. 354/432 |
| 5,559,629 A | | 9/1996 | Sheets et al. ................ 359/364 |
| 5,666,202 A | * | 9/1997 | Kyrazis ....................... 356/614 |
| 5,843,657 A | * | 12/1998 | Liotta et al. .................... 435/6 |
| 5,859,699 A | | 1/1999 | Baer et al. ................... 356/246 |
| 5,876,327 A | * | 3/1999 | Tsuyuki et al. .............. 600/112 |
| 5,972,667 A | | 10/1999 | Conia et al. .............. 435/173.2 |
| 5,973,844 A | * | 10/1999 | Burger ........................ 359/622 |
| 5,985,085 A | | 11/1999 | Baer et al. ................... 156/285 |
| 6,005,916 A | | 12/1999 | Johnson et al. ................ 378/87 |
| 6,008,945 A | | 12/1999 | Fergason ..................... 359/630 |
| 6,088,097 A | | 7/2000 | Uhl ............................. 356/318 |
| 6,100,051 A | | 8/2000 | Goldstein et al. .......... 435/40.5 |
| 6,124,974 A | | 9/2000 | Burger ........................ 359/621 |
| 6,128,068 A | | 10/2000 | Suzuki et al. ................. 355/53 |
| 6,157,446 A | | 12/2000 | Baer et al. ................... 356/244 |
| 6,159,681 A | | 12/2000 | Zebala ........................... 435/4 |
| 6,184,973 B1 | | 2/2001 | Baer et al. .................... 356/36 |
| 6,195,213 B1 | | 2/2001 | Omura et al. ............... 359/727 |
| 6,208,139 B1 | * | 3/2001 | Foo et al. .................... 324/309 |
| 6,211,484 B1 | | 4/2001 | Kaplan et al. ......... 219/121.68 |
| 6,215,550 B1 | | 4/2001 | Baer et al. .................... 356/36 |
| 6,512,576 B1 | * | 1/2003 | Baer et al. .................... 356/36 |

OTHER PUBLICATIONS

Holst, Gerald C., "Image Quality: Does Your Detector Match Your Optics? Understanding the term "resolution" for both optics and detectors provides a solid basis for designing imaging systems." Photonics Spectra, Jan. 1999, pp. 144–146.

Casasesnt, David, "Performing Image Analysis With Optical Pattern Recognition," The Photonics Design and Applications Handbook, 1998, pp. 158–161.

Mukundakrishnan, Bharath, "Design for Visually Servoed Microassembly," Advanced Microsystems Laboratory, Department of Mechanical Engineering, University of Minnesota 2000.

"Using your microscope, high magnifications with an oil–immersion objective." http://www.fishdoc.co.uk/microscope/micro04.htm Jul. 9, 2001.

Melles Griot, Optical Systems, Machine Vision Product Guide, USA, 1998.

* cited by examiner

Primary Examiner—Tu T. Nguyen
(74) Attorney, Agent, or Firm—Amin & Turocy, LLP

(57) ABSTRACT

Improved laser capture microdissection systems and related methods are provided by using an imaging system for imaging the tissue sample from which a cell sample is to be obtained, the imaging system comprising a sensor having one or more receptors, and an image transfer medium to scale the one or more receptors to an object field of view.

20 Claims, 10 Drawing Sheets

| | 750 x – 1500 x nominal Effective Magnification | 1500x – 2500 x nominal Effective Magnification | 2500x – 5000 x nominal Effective Magnification |
|---|---|---|---|
| Effective Resolved Magnification | | | |
| Working Distance (mm) | 13.0 mm DRY space | 5.0 mm DRY space | 0.5 mm DRY space |
| Absolute Spatial Resolution (nanometers) | 800 nm typical - | 400 nm typical - | 200 nm typical - |
| Spatial Field Of View (mm) | 1.00 mm | 0.500 mm | 0.250 mm |
| Conventional Objective employed | 10 x DRY | 20 x DRY | 40 x DRY |
| Eyepiece (view or photographic) | NOT EMPLOYED (DIGITAL DISPLAY) | NOT EMPLOYED (DIGITAL DISPLAY) | NOT EMPLOYED (DIGITAL DISPLAY) |
| Depth Of Field (microns - μ) | 16 μm | 6.25 μm | 2.5 μm |
| Absolute Spatial Resolution per Pixel at Sensor (nanometers) | 800 nm typical - | 400 nm typical - | 200 nm typical - |

Fig. 5

MICRODISSECTION OPTICAL SYSTEM

FIELD OF THE INVENTION

The present invention generally relates to an optical system that facilitates laser capture microdissection techniques.

BACKGROUND OF THE INVENTION

Many diseases are identified by examining tissue biopsies to identify unusual cells. Examples include cancer. One problem with examining such tissue biopsies is that there is room for improvement in extracting the cells of interest from the surrounding tissue. Currently, investigators must attempt to manually extract, or microdissect, cells of interest either by attempting to mechanically isolate them with a manual tool or through a convoluted process of isolating and culturing the cells. These approaches can be tedious, time-consuming, and/or inefficient.

A new technique that extracts a small cluster of cells from a tissue sample in a matter of seconds is gaining attention. The technique is called laser capture microdissection. Laser capture microdissection is a straight forward technique which integrates a standard laboratory microscope with a low-energy laser and a transparent thermoplastic film.

Laser capture microdissection involves providing a tissue sample typically on a slide under observation in a microscope. The tissue is contacted with a selectively activated surface which could be activated to provide selective regions thereof with adhesive properties. The tissue sample is visualized through the microscope and at least one portion of the tissue sample which is to be extracted is identified. Thereafter, the selectively activated surface is activated, typically by a laser routed through a fiber optic being directed onto the selectively activated surface in the footprint of the desired tissue. This is done while a region of selectively activated surface is in contact with the portion of the tissue sample selected. The activated region of the selectively activated surface adheres to that portion of the tissue sample. The activated surface is then separated from the tissue sample while maintaining adhesion between the activated region of selectively activated surface and the portion of the tissue sample. The portion of the tissue sample is extracted from the remaining portion of the tissue sample.

One purpose of the laser capture microdissection technique is to provide a simple method for the procurement of selected human cells from a heterogeneous population contained on a typical histopathology biopsy slide. By taking only these target cells directly from the tissue sample, scientists can immediately examine the target cells. Moreover, gene and enzyme activity of the target cells can be analyzed using other research tools. In this connection, procedures such as polymerase chain reaction amplification of DNA and RNA, and enzyme recovery from the tissue sample are useful. No limitations currently exist in the ability to amplify DNA or RNA from tumor cells extracted with laser capture microdissection.

Currently available optical systems or microscopes are not well suited for facilitating laser capture microdissection. For example, currently available optical systems have narrow fields of view, small depth of field, and small working distances under high magnification. The narrow field of view makes it difficult to identify a precise location for irradiation. The small depth of field makes it difficult to monitor the progress of irradiation. The small working distance makes it difficult to manipulate and handle the tissue sample.

Many microscopes are designed to provide images of certain quality to the human eye through an eyepiece. Connecting a Machine Vision Sensor, such as a Charge Coupled Device (CCD) sensor, to the microscope so that an image may be viewed on a monitor presents difficulties because the image quality decreases, as compared to an image viewed by a human eye through an eyepiece. As a result, optical systems for laser capture microdissection often require the careful attention of a technician monitoring the process through an eyepiece.

SUMMARY OF THE INVENTION

The direct access to cells provided by laser capture microdissection may lead to improvements in the understanding of the molecular basis of cancer and other diseases, helping to lay the groundwork for earlier and more precise disease detection. The optical system and methods of the present invention furthers this understanding by enabling at least one of finer and more precise laser capture microdissection tissue sampling; greater working distances thereby not interfering with manipulation of the tissue samples; flexibility in laser spot positioning and sizing; closed circuit, web based, and remote monitoring of laser capture microdissection procedures; immediate examination of tissue samples; and automated process control of laser capture microdissection systems and methods.

BRIEF SUMMARY OF THE DRAWINGS

FIG. 5 is a chart illustrating exemplary performance specifications in accordance with an aspect of the present invention.

DETAILED DESCRIPTION OF THE INVENTION

Figure 1:
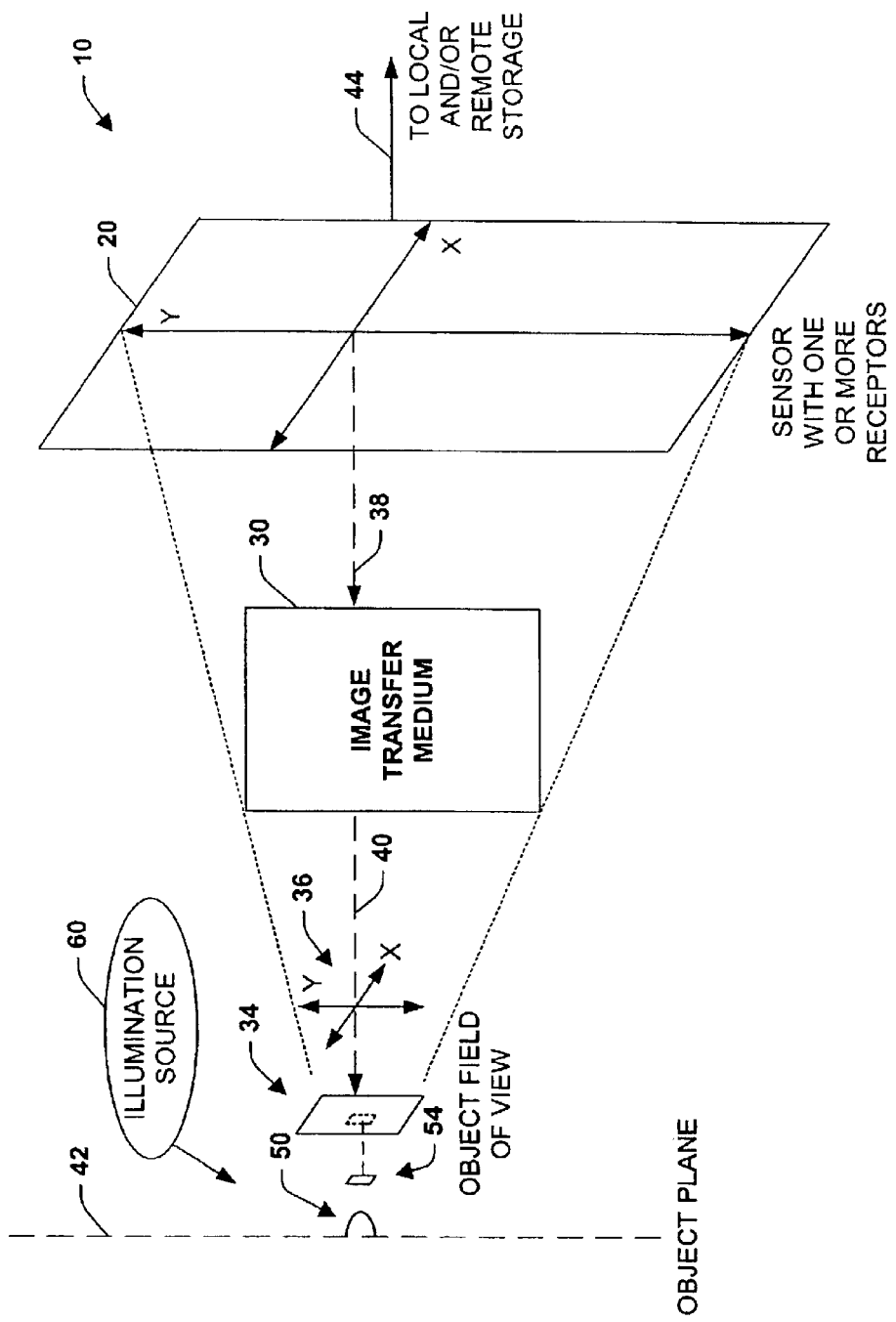
FIG. 1 is a schematic block diagram illustrating a laser capture microdissection imaging system in accordance with an aspect of the present invention.

A novel imaging system that provides high effective resolved magnification and high spatial resolution among other features and laser capture microdissection components and methods are combined to provide improved laser capture microdissection systems and methods. The laser capture microdissection systems and methods of the present invention are valuable tools for procuring pure cell samples from tissue samples.

In laser capture microdissection systems and methods in accordance with the present invention, an operator views an image of a tissue biopsy section mounted on a slide developed using a sensor matched optics imaging system.

The tissue sample is typically mounted on a standard glass histopathology slide, which may contain groups of the same or different types of cells. Laser capture microdissection is effective in extracting cells in any tissue sample.

A transfer film, typically a thermoplastic film, is placed over and in contact with the tissue biopsy section. The thermoplastic film is capable of locally melting while remaining unchanged in other regions, acquiring adhesion properties in the melted region, and adhering to a small portion of a tissue sample (corresponding to the melted region) while the remaining unchanged portions of the film do not adhere to the sample. An example of a thermoplastic transfer film is a 100 micron thick ethyl vinyl acetate film available from Electroseal Corporation of Pompton Lakes, N.J. (type E540). The film is typically chosen to have a relatively low melting point, such as about 100° C. or less including about 90° C. or less, about 80° C. or less, and about 70° C. or less.

Upon identifying a group of cells of interest within the tissue section, the operator positions them in a target area of the image field of the imaging system and then generates a pulse from a laser. In one embodiment, a laser having an intensity of about 10 milliwatts (mW) or more and about 250 W or less, a pulse duration of about 0 seconds or more and about 1 second or less may be employed. In another embodiment, a laser having an intensity of about 50 mW or more and about 100 W or less, a pulse duration of about 1 millisecond or more and about 500 milliseconds or less may be employed. In yet another embodiment, a laser having an intensity of about 10 mW or more and about 50 W or less, a pulse duration of about 10 milliseconds or more and about 100 milliseconds or less may be employed.

Examples of lasers or excitation sources include carbon dioxide lasers, other gas lasers, NdYAG lasers, solid state lasers, ion lasers, diode lasers, diode pumped lasers, dye lasers, semiconductor lasers, and the like. The wavelength employed typically depends upon the identity of the laser. Any wavelength capable of locally melting the thermoplastic film without substantially damaging the tissue sample may be employed.

The size (cross-section or diameter) of the beam spot formed by the laser on the thermoplastic film is sufficient to obtain a tissue section of desired size. In one embodiment, the size of the beam spot is about 0.25 $\mu$m or more and about 250 $\mu$m or less. In another embodiment, the size of the beam spot is about 1 $\mu$m or more and about 100 $\mu$m or less. In yet another embodiment, the size of the beam spot is about 5 $\mu$m or more and about 50 $\mu$m or less.

Changing the beam diameter permits the size of the portion of the tissue sample that is acquired to be adjusted. Given a tightly focused initial condition, the beam size can be increased by defocusing. Conversely, given a defocused initial condition, the beam size can be decreased by focusing. The change in focus can be in fixed amounts. The change in focus can be obtained by means of indents on a movable lens mounting and/or by means of optical glass steps. In any event, increasing/decreasing the optical path length is the effect that is needed to alter the focus of the beam, thereby altering the spot size. For example, inserting a stepped glass prism into the laser beam path so the beam strikes one step tread changes the optical path length and alters the spot size.

The laser pulse causes localized heating of the plastic film as it passes through it, imparting to the plastic film an adhesive property. The cells then stick to the localized adhesive area of the plastic tape directly above them, whereupon the cells are immediately extracted and ready for analysis. Because of the small diameter of the laser beam, extremely small cell clusters may be microdissected from a tissue section.

A typical tissue biopsy sample may consist of a 2.5 to 20 micron slice of tissue that is placed on a glass microscope slide using techniques known in the field of pathology, although larger or smaller tissue samples may be employed. This tissue slice is a cross section of the body organ that is being studied. The tissue may consist of a variety of different types of cells. Often a pathologist desires to remove only a small portion of the tissue for further analysis. Examples of tissue samples include kidney glomeruli, in situ breast carcinoma, atypical ductal hyperplasia of the breast, prostatic interepithielial neoplasia, and lymphoid follicles, among many others.

In other words, laser capture microdissection employs a thermoplastic transfer film that is placed on top of the tissue sample. This film is manufactured containing dyes that are chosen to selectively absorb in the region of the spectrum overlapping the emission region of common laser diodes (or any of the above mentioned excitation sources). When the film is exposed to the focused laser beam the exposed region is heated by the laser and melts, adhering to the tissue in the region that is exposed. The film is then lifted from the tissue and the selected portion of the tissue is removed with the film.

Examples of various laser capture microdissection techniques to which the sensor matched optics imaging system of the present invention can be applied include those described in Laser Capture Microdissection, Science, Volume 274, Number 5289, Issue 8, pp 998–1001, published in 1996; U.S. Pat. Nos. 6,251,516; 6,251,467; 6,215,550; 6,204,030; 6,184,973; 6,157,446; 6,100,051; 6,010,888; 5,985,085; 5,972,667; 5,859,699; 5,843,657; and 5,843,644, the entire contents of which are incorporated herein by reference.

According to one aspect of the present invention, a k-space filter is provided that can be configured from an image transfer medium such as optical media that correlates image sensor receptors to an object field of view. A variety of illumination sources can also be employed to achieve one or more operational goals and for versatility of application. The k-space design of the imaging system of the present invention promotes capture and analysis (e.g., automated and/or manual) of images having a high Field Of View (FOV) at substantially high Effective Resolved Magnification as compared to conventional laser capture microdissection microscopes. This can include employing a small Numerical Aperture (NA) associated with lower magnification objective lenses to achieve very high Effective Resolved Magnification. As a consequence, images having a substantially large Depth Of Field (DOF) at very high Effective Resolved Magnification are also realized. The k-space design also facilitates employment of homogeneous illumination sources that are substantially insensitive to changes in position, thereby improving laser capture microdissection methods.

According to another aspect of the present invention, an objective lens to tissue sample or object distance (e.g., Working Distance) can be maintained in operation at low and high power effective resolved magnification imaging, wherein typical spacing can be achieved at about 0.1 mm or more and about 20 mm or less, as opposed to conventional microscopic systems which can require significantly smaller (as small as 0.01 mm) tissue sample to objective lens distances for comparable (e.g., similar order of magnitude) Effective Resolved Magnification values. In another embodiment, the Working Distance is about 0.5 mm or more and about 10 mm or less. It is to be appreciated that the present invention is not limited to operating at the above working distances. In many instances the above working distances are employed, however, in some instances, smaller or larger distances are employed. It is further noted that oil immersion or other Index of Refraction matching media or fluids for objective lenses are generally not required (e.g., substantially no improvement to be gained) at one or more effective image magnification levels of the present invention yet, still exceeding effective resolved magnification levels achievable in conventional laser capture microdissection microscopic optical design variations including systems employing "infinity-corrected" objective lenses.

The k-space design of the laser capture microdissection imaging system of the present invention defines that a small "Blur Circle" or diffraction limited point/spot at the object plane is determined by parameters of the design to match image sensor receptors or pixels with a substantially one-to-one correspondence by "unit-mapping" of object and image spaces for associated object and image fields. This enables the improved performance and capabilities of the present invention. One possible theory of the k-space design results from the mathematical concept that since the Fourier Transform of both an object and an image is formed in k-space (also called "reciprocal space"), the sensor should be mapped to the object plane in k-space via optical design techniques and component placement in accordance with the present invention. It is to be appreciated that a plurality of other transforms or models can be utilized to configure and/or select one or more components in accordance with the present invention. For example, wavelet transforms, LaPlace (s-transforms), z-transforms as well as other transforms can be similarly employed.

The k-space design methodology is unlike conventional laser capture microdissection optical systems designed according to geometric, paraxial ray-trace and optimization theory, since the k-space optimization facilitates that the spectral components of the object (tissue sample) and the image are the same in k-space, and thus quantized. Therefore, there are substantially no inherent limitations imposed on a Modulation Transfer Function (MTF) describing contrast versus resolution and absolute spatial resolution in the present invention. Quantization, for example, in k-space yields a substantially unitary Modulation Transfer Function not realized by conventional systems. It is noted that high MTF, Spatial Resolution, and effective image magnification can be achieved with much lower magnification objective lenses with desirable lower Numerical Apertures (e.g., generally less than about 50× and at a numerical aperture generally less than about 0.7) through "unit-mapping" of projected pixels in an "Intrinsic Spatial Filter" provided by the k-space design.

If desired, "infinity-corrected" objectives can be employed with associated optical component and illumination, as well as spectrum varying components, polarization varying components, and/or contrast or phase varying components. These components can be included in an optical path-length between an objective and the image lens within an "infinity space". Optical system accessories and variations can thus be positioned as interchangeable modules in this geometry. The k-space design, in contrast to conventional laser capture microdissection microscopic imagers that utilize "infinity-corrected" objectives, enables the maximum optimization of the infinity space geometry by the "unit-mapping" concept. This implies that there is generally no specific limit to the number of additional components that can be inserted in the "infinity space" geometry as in conventional laser capture microdissection microscopic systems that typically specify no more than 2 additional components without optical correction.

The present invention also enables a "base-module" design that can be configured and reconfigured in operation for a plurality of different applications if necessary to employ either transmissive or reflected illumination, if desired. This includes substantially all typical machine vision illumination schemes (e.g., darkfield, brightfield, phase-contrast), and other microscopic transmissive techniques (Kohler, Abbe), in substantially any offset and can include Epi illumination. The systems of the present invention can be employed in a plurality of opto-mechanical designs that are robust since the k-space design is substantially not sensitive to environmental and mechanical vibration and thus generally does not require heavy structural mechanical design and isolation from vibration associated with conventional laser capture microdissection microscopic imaging instruments. Other features can include digital image processing, if desired, along with storage (e.g., local database, image data transmissions to remote computers for storage/analysis) and display of the images produced in accordance with the present invention (e.g., computer display, printer, film, and other output media). Remote signal processing of image data can be provided, along with communication and display of the image data via associated data packets that are communicated over a network or other medium, for example.

Referring initially to FIG. 1, a laser capture microdissection imaging system 10 is illustrated in accordance with an aspect of the present invention. The imaging system 10 includes a sensor 20 having one or more receptors such as pixels or discrete light detectors (See e.g., illustrated below in FIG. 3) operably associated with an image transfer medium 30. The image transfer medium 30 is adapted or configured to scale the proportions of the sensor 20 at an image plane established by the position of the sensor 20 to an object field of view illustrated at reference numeral 34. A planar reference 36 of X and Y coordinates is provided to illustrate the scaling or reduction of the apparent or virtual size of the sensor 20 to the object field of view 34. Direction arrows 38 and 40 illustrate the direction of reduction of the apparent size of the sensor 20 toward the object field of view 34.

The object field of view 34 established by the image transfer medium 30 is related to the position of an object plane 42 that includes one or more tissue samples (not shown). It is noted that the sensor 20 can be substantially any size, shape and/or technology (e.g., digital sensor, analog sensor, CCD sensor, CMOS sensor, Charge Injection Device (CID) sensor, an array sensor, a linear scan sensor) including one or more receptors of various sizes and shapes, the one or more receptors being similarly sized or proportioned on a respective sensor to be responsive to light (e.g., visible, non-visible) received from the items under examination in the object field of view 34. As light is received from the object field of view 34, the sensor 20 provides an output 44 that can be directed to a local or remote storage such as a memory (not shown) and displayed from the memory via a computer and associated display, for example, without substantially any intervening digital processing (e.g., straight bit map from sensor memory to display), if desired. It is noted that local or remote signal processing of the image data received from the sensor 20 can also occur. For example, the output 44 can be converted to electronic data packets and transmitted to a remote system over a network for further analysis and/or display. Similarly, the output 44 can be stored in a local computer memory before being transmitted to a subsequent computing system for further analysis and/or display.

The scaling provided by the image transfer medium 30 is determined by a novel k-space configuration or design within the medium that promotes predetermined k-space frequencies of interest and mitigates frequencies outside the predetermined frequencies. This has the effect of a bandpass filter of the spatial frequencies within the image transfer medium 30 and notably defines the laser capture microdissection imaging system 10 in terms of resolution rather than magnification. As will be described in more detail below, the resolution of the imaging system 10 determined by the k-space design promotes a plurality of features in a displayed or stored image such as having high effective resolved magnification, high spatial resolution, large depth of field, larger working distances, and a unitary Modulation Transfer Function as well as other features that facilitate laser capture microdissection methods.

In order to determine the k-space frequencies, a "pitch" or spacing is determined between adjacent receptors on the sensor 20, the pitch related to the center-to-center distance of adjacent receptors and about the size or diameter of a single receptor. The pitch of the sensor 20 defines the Nyquist "cut-off" frequency band of the sensor. It is this frequency band that is promoted by the k-space design, whereas other frequencies are mitigated. In order to illustrate how scaling is determined in the imaging system 10, a small or diffraction limited spot or point 50 is illustrated at the object plane 42. The diffraction limited point 50 represents the smallest resolvable object determined by optical characteristics within the image transfer medium 30 and is described in more detail below. A scaled receptor 54, depicted in front of the field of view 34 for exemplary purposes, and having a size determined according to the pitch of the sensor 20, is matched or scaled to be about the same size in the object field of view 34 as the diffraction limited point 50.

In other words, the size of any given receptor at the sensor 20 is effectively reduced in size via the image transfer medium 30 to be about the same size (or matched in size) to the size of the diffraction limited point 50. This also has the effect of filling the object field of view 34 with substantially all of the receptors of the sensor 20, the respective receptors being suitably scaled to be similar in size to the diffraction limited point 50. As will be described in more detail below, the matching/mapping of sensor characteristics to the smallest resolvable object or point within the object field of view 34 defines the imaging system 10 in terms of absolute spatial resolution and profoundly enhances the operating performance of the system.

An illumination source 60 can be provided with the present invention in order that photons can be emitted from objects in the field of view 34 to enable activation of the receptors in the sensor 20. It is noted that the present invention can potentially be employed without an illumination source 60 if potential self-luminous objects (e.g., fluorescent tissue sample) emit enough radiation to activate the sensor 60. Light Emitting Diodes, however, provide an effective illumination source 60 in accordance with the present invention. Substantially any illumination source 60 can be applied including coherent and non-coherent sources, visible and non-visible wavelengths. However, for non-visible wavelength sources, the sensor 20 would also be suitably adapted. For example, for an infrared or ultraviolet source, an infrared or ultraviolet sensor 20 would be employed, respectively. Other illumination sources 60 can include wavelength-specific lighting, broad-band lighting, continuous lighting, strobed lighting, Kohler illumination, Abbe illumination, phase-contrast illumination, darkfield illumination, brightfield illumination, and Epi illumination. Transmissive or reflective lighting techniques can also be applied.

Figure 2:
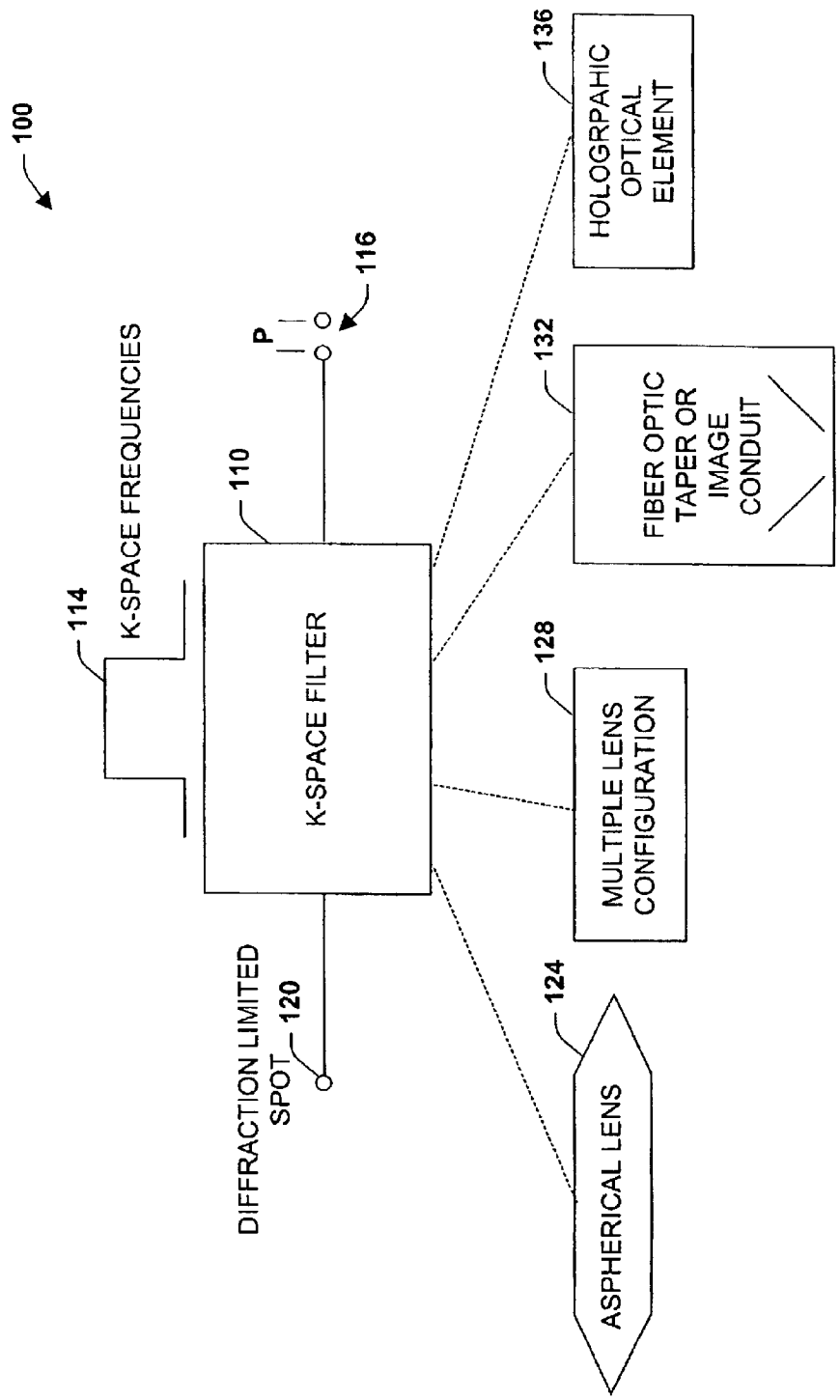
FIG. 2 is a diagram illustrating a k-space system design in accordance with an aspect of the present invention.

Referring now to FIG. 2, a system 100 illustrates an image transfer medium 30 in accordance with an aspect of the present invention. The image transfer medium 30 depicted in FIG. 1 can be provided according to the k-space design concepts described above and more particularly via a k-space filter 110 adapted, configured and/or selected to promote a band of predetermined k-space frequencies 114 and to mitigate frequencies outside of this band. This is achieved by determining a pitch "P"—which is the distance between adjacent receptors 116 in a sensor (not shown) and sizing optical media within the filter 110 such that the pitch "P" of the receptors 116 is matched in size with a diffraction-limited spot 120. The diffraction-limited spot 120 can be determined from the optical characteristics of the media in the filter 110. For example, the Numerical Aperture of an optical medium such as a lens defines the smallest object or spot that can be resolved by the lens. The filter 110 performs a k-space transformation such that the size of the pitch is effectively matched, "unit-mapped", projected, correlated, and/or reduced to the size or scale of the diffraction limited spot 120.

It is to be appreciated that a plurality of novel optical configurations can be provided to achieve the k-space filter 110. One such configuration can be provided by an aspherical lens 124 adapted such to perform the k-space transformation and reduction from sensor space to object space. Yet another configuration can be provided by a multiple lens arrangement 128, wherein the lens combination is selected to provide the filtering and scaling. Still yet another configuration can employ a fiber optic taper 132 or image conduit, wherein multiple optical fibers or array of fibers are configured in a funnel-shape to perform the mapping of the sensor to the object field of view. It is noted that the fiber optic taper 132 is generally in physical contact between the sensor and the object under examination (e.g., contact with microscope slide). Another possible k-space filter 110 arrangement employs a holographic or other diffractive or phase optical element 136, wherein a substantially flat optical surface is configured via a hologram or other diffractive or phase structure (e.g., computer-generated, optically generated, and/or other method) to provide the mapping in accordance with the present invention.

The k-space optical design as enabled by the k-space filter 110 is based upon the "effective projected pixel-pitch" of the sensor, which is a figure derived from following ("projecting") the physical size of the sensor array elements back through the optical system to the object plane. In this manner, conjugate planes and optical transform spaces are matched to the Nyquist cut-off of the effective receptor or pixel size. This maximizes the effective image magnification and the Field Of View as well as the Depth Of Field and the Absolute Spatial Resolution. Thus, a novel application of optical theory is provided that does not rely on conventional geometric optical design parameters of paraxial ray-tracing which govern conventional optics and imaging combinations. This can further be described in the following manner.

A Fourier transform of an object and an image is formed (by an optical system) in k-space (also referred to as "reciprocal-space"). It is this transform that is operated on for image optimization by the k-space design of the laser capture microdissection imaging system of the present invention. For example, the optical media employed in the present invention can be designed with standard, relatively non-expensive "off-the-shelf" components having a configuration which defines that the object and image space are "unit-mapped" or "unit-matched" for substantially all image and object fields. A small Blur-circle or diffraction-limited spot 120 at the object plane is defined by the design to match the pixels in the image plane (e.g., at the image sensor of choice) with substantially one-to-one correspondence and thus the Fourier transforms of pixelated arrays can be matched. This implies that, optically by design, the Blur-circle is scaled to be about the same size as the receptor or pixel pitch. The laser capture microdissection imaging system of the present invention is defined such that it constructs an Intrinsic Spatial Filter such as the k-space filter 110. Such a design definition and implementation enables the spectral components of both the object and the image in k-space to be about the same or quantized. This also defines that the Modulation Transfer Function (MTF) (the comparison of contrast to spatial resolution) of the sensor is matched to the MTF of the object Plane.

Figure 3:
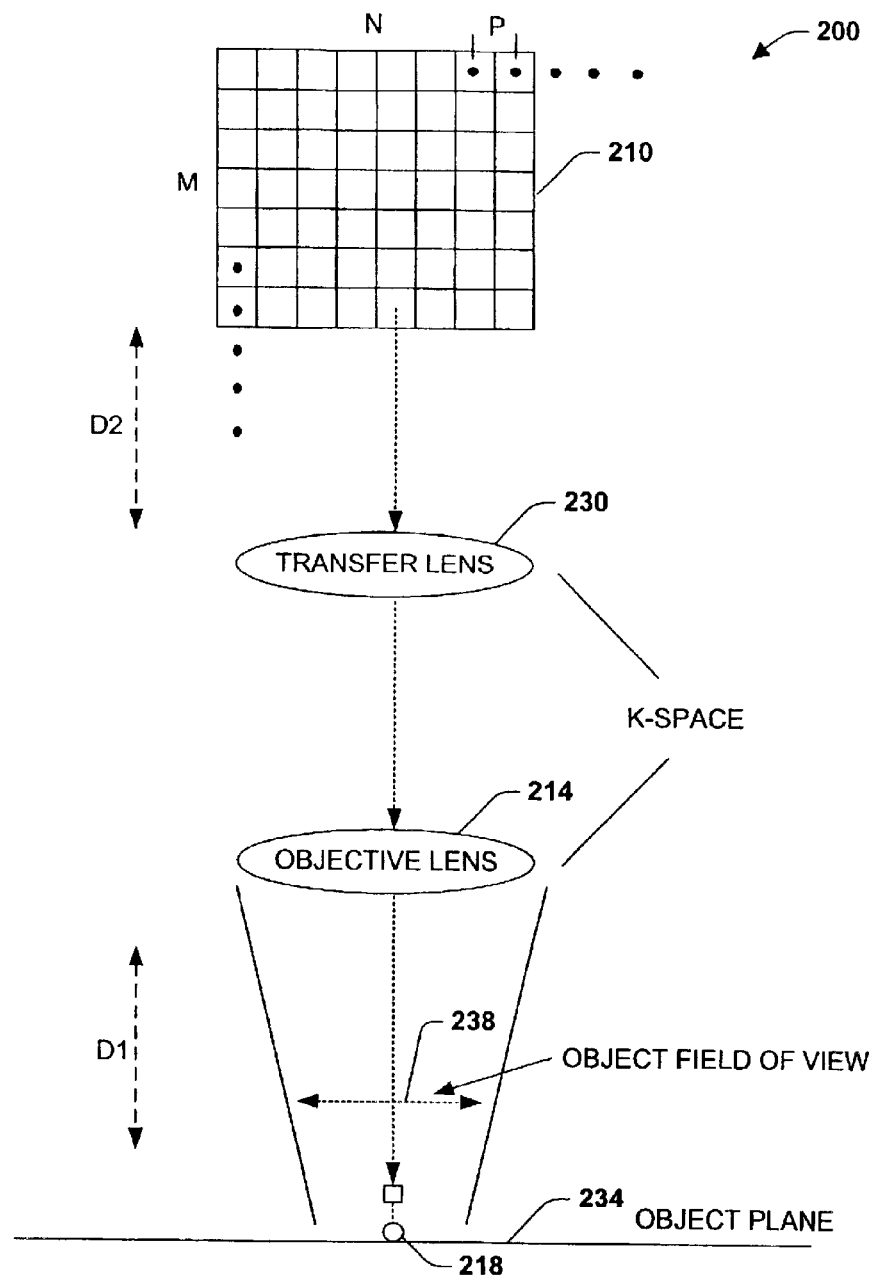
FIG. 3 is a diagram of an exemplary system illustrating sensor receptor matching in accordance with an aspect of the present invention.

Turning now to FIG. 3, a multiple lens system 200 illustrates an exemplary unit-mapping design in accordance with an aspect of the present invention. The system 200 includes an M by N array 210 of sensor pixels (e.g., 640×480, 512×512, 1024×1280, etc.), having M rows and N columns, M and N being integers respectively. Although a rectangular array 210 having square pixels is depicted, it is to be appreciated as noted above, the array 210 can be substantially any shape such as circular, elliptical, hexagonal, rectangular, etc. wherein respective pixels within the array 210 can also be substantially any shape or size, the pixels in any given array 210 being similarly sized and spaced. Unit-mapping can be determined for a plurality of sensors and lens combinations. For example, a substantially-wide diameter achromatic objective lens 214 (e.g., about 10 millimeters or more to about 100 millimeters or less in diameter) can be selected to preserve k-space frequencies of interest and having a Numerical Aperture capable of resolving diffraction-limited spots 218 of about 1 micron, for example, and having a focal length "D1" of about 1 centimeter. It is noted that the dimensions selected for the system 200 are provided for exemplary purposes to facilitate understanding of the concepts described above. Thus, for example, if an objective lens 214 were selected that is capable of resolving diffraction limited spots 218 having other dimensions (e.g., about 0.2, about 0.3, about 0.4, about 0.6 microns, etc.), then a different lens, sensor and/or lens/sensor combination is selected to provide the scaling and/or unit-mapping in accordance with the present invention.

In order to provide unit-mapping according to this example, and assuming for purposes of illustration that the sensor array 210 provides a pixel pitch "P" of about 10 microns, a relationship is to be determined between an achromatic transfer lens 230 and the objective lens 214 such that a reduction is achieved from sensor space defined at the array 210 to object space defined at an object plane 234 and thus, scaling respective pixels from the array 210 to about the size of the diffraction limited spot 218. It is noted that substantially all of the pixels are projected into an object field of view depicted at reference numeral 238 and defined by the objective lens 214, wherein respective pixels are sized to about the dimensions of the diffraction limited spot 218. The reduction in size of the array 210 and associated pixels can be achieved by selecting the transfer lens to have a focal length "D2" (from the array 210 to the transfer lens 230) of about 10 centimeters in this example. In this manner, the pixels in the array 210 are effectively reduced in size to about 1 micron per pixel, thus matching the size of the diffraction limited spot 218 and filling the object field of view 238 with a "virtually-reduced" array of pixels 210.

As illustrated in FIG. 3, k-space is defined as the region between the objective lens 214 and the transfer lens 230. It is to be appreciated that substantially any optical media, lens type and/or lens combination that reduces, maps and/or projects the sensor array 210 to the object field of view 238 in accordance with unit or k-space mapping as has been previously described is within the scope of the present invention. To illustrate the novelty of the exemplary lens/sensor combination depicted in FIG. 3, it is noted that conventional laser capture microdissection objective lenses, sized according to conventional geometric paraxial ray techniques, are generally sized according to the magnification, Numeric Aperture, focal length and other parameters provided by the objective. Thus, the objective lens would be sized with a greater focal length than subsequent lenses that approach or are closer to the sensor (or eyepiece in conventional microscope) in order to provide magnification of small objects. This can result in magnification of the small objects at the object plane being projected as a magnified image of the objects across "portions" of the sensor and results in known detail blur (e.g., Rayleigh diffraction and other limitations in the optics), empty magnification problems, and Nyquist aliasing among other problems at the sensor. The k-space design of the laser capture microdissection imaging system of the present invention operates as an alternative to geometric paraxial ray design principles. As illustrated in FIG. 3, the objective lens 214 and the transfer lens 230 operate to provide a reduction in size of the sensor array 210 to the object field of view 238 as demonstrated by the relationship of the lenses.

Figure 4:
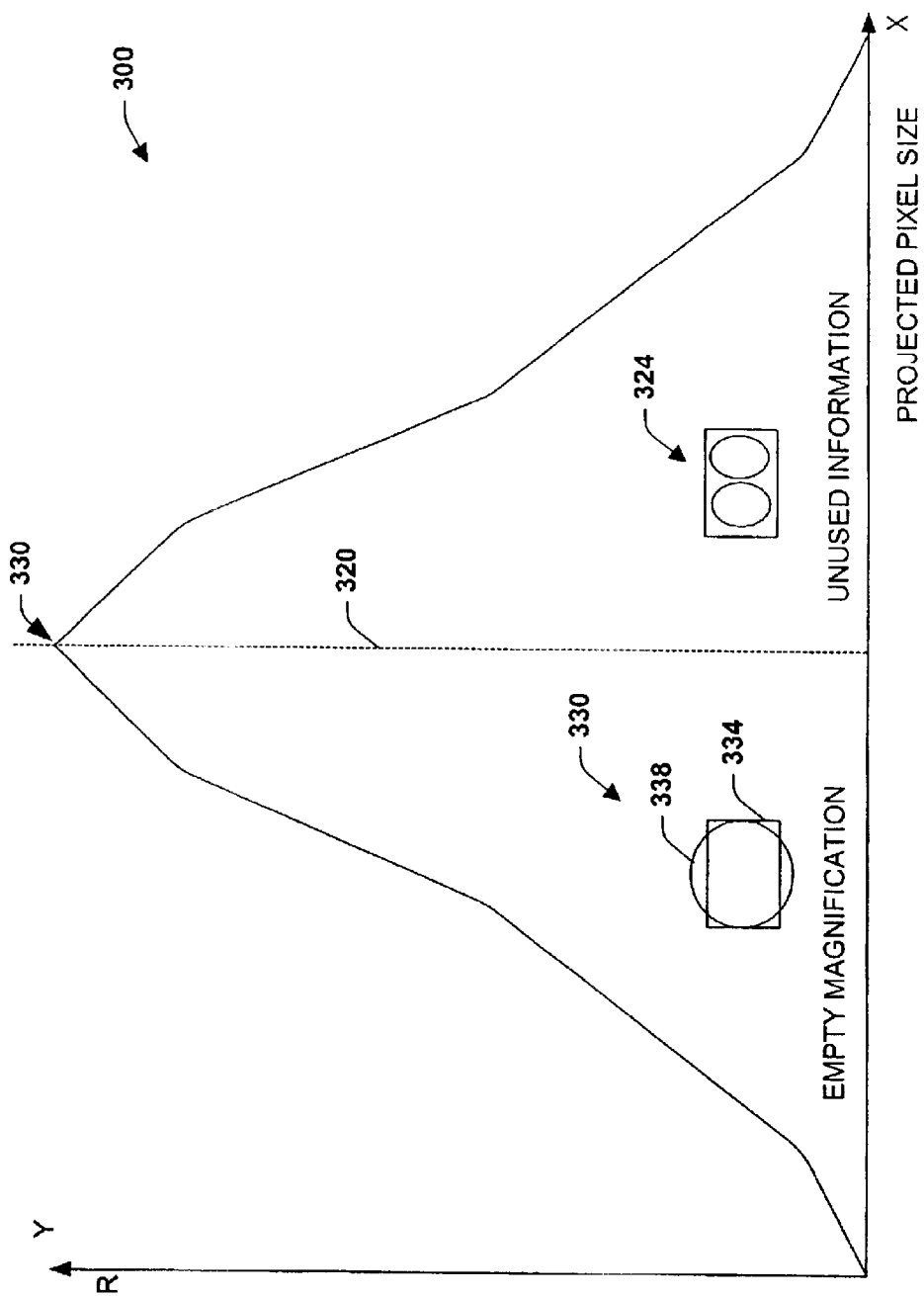
FIG. 4 is a graph illustrating sensor matching considerations in accordance with an aspect of the present invention.

Referring now to FIG. 4, a graph 300 illustrates mapping characteristics and comparison between projected pixel size on the X axis and diffraction-limited spot resolution size "R" on the Y axis. At the apex 310 of the graph 300, a unit mapping between projected pixel size and diffraction-limited spot size occurs which is the optimum relationship in accordance with the laser capture microdissection imaging system of the present invention. It is noted that the objective lens 214 depicted in FIG. 3 need generally not be selected such that the diffraction-limited size "R" of the smallest resolvable objects is smaller than a projected pixel size. If so, "economic waste" can occur wherein more precise information is lost (e.g., selecting an object lens more expensive than required). This is illustrated to the right of a dividing line 320 at reference 324 depicting a projected pixel larger that two smaller diffraction spots. If an objective is selected with diffraction-limited performance larger than the projected pixel size, blurring and empty magnification can occur. This is illustrated to the left of line 320 at reference numeral 330, wherein a projected pixel 334 is smaller than a diffraction-limited object 338. It is to be appreciated, however, that even if substantially one-to-one correspondence is not achieved between projected pixel size and the diffraction-limited spot, a system can be configured with less than optimum matching (e.g., about 0.1% or more, about 1% or more, about 2% or more, about 5% or more, about 20% or more, about 95% or more down from the apex 330 on the graph 300 to the left or right of the line 320) and still provide suitable performance. Thus, less than optimal matching is intended to fall within the spirit and the scope of present invention. It is further noted that the diameter of the lenses in the system as illustrated in FIG. 3, for example, can be sized such that when a Fourier Transform is performed from object space to sensor space, spatial frequencies of interest that are in the band pass region described above (e.g., frequencies utilized to define the size and shape of a pixel) are substantially not attenuated. This generally implies that larger diameter lenses (e.g., about 10 to about 100 millimeters) are typically selected to mitigate attenuation of the spatial frequencies of interest.

FIG. 5 illustrates a chart 400 of exemplary and typical performance parameters that can be achieved via the k-space design of the laser capture microdissection imaging system of the present invention employing standard, low-cost, and commercially available components such as dry objective lenses, a 1024×1280 sensor, LED illumination source wavelengths selected at about twice the wavelength of the desired resolution (e.g., for 200 nanometer resolution, 400 nanometer light source selected), and a straight bit map from sensor to image display without intervening signal processing. Custom components can be alternatively fabricated. As can be observed, effective resolved magnifications of about 5000 times can be achieved at an absolute spatial resolution of about 200 nanometers in a typical non-optimized system. As used herein, the term "Effective Resolved Magnification" is utilized to objectively compare the relative apparent image size and Absolute Spatial Resolution of the laser capture microdissection imaging system of the present invention with conventional laser capture microdissection microscopic imaging systems.

In one embodiment, the images produced in accordance with the present invention have a depth of field of about 1 micron or more and about 50 microns or less at an Effective Resolved Magnification of about 750 times or more and about 5000 times or less. In another embodiment, the images produced in accordance with the present invention have a depth of field of about 10 microns or more and about 40 microns or less at an Effective Resolved Magnification of about 750 times or more and about 2500 times or less.

In one embodiment, the images produced in accordance with the present invention have an effective resolved magnification of about 2500 times or more and about 5000 times or less while providing a spatial field of view of about 0.250 millimeters or less. In another embodiment, the images produced in accordance with the present invention have an effective resolved magnification of about 500 times or more and about 2500 times or less while providing a spatial field of view of about 0.2 millimeters or less.

Figure 6:
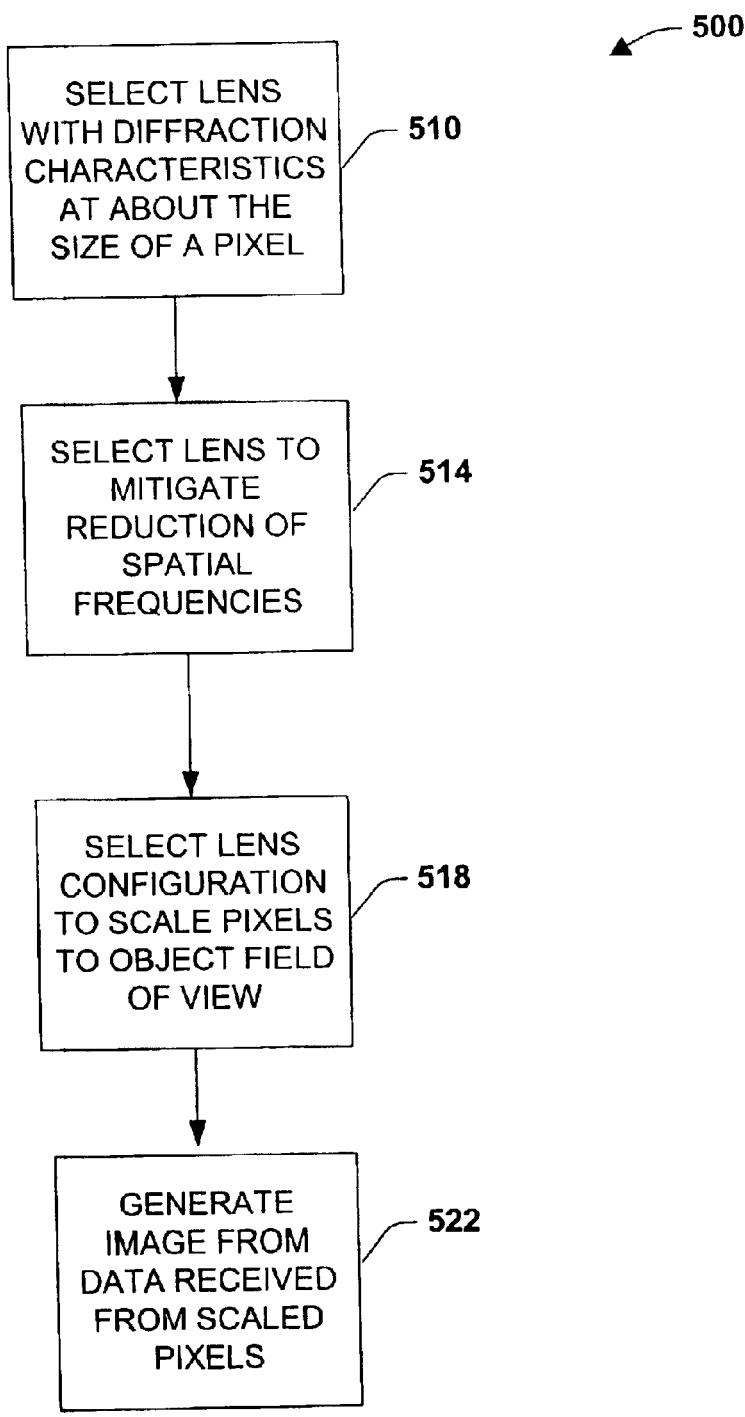
FIG. 6 is a flow diagram illustrating a laser capture microdissection imaging methodology in accordance with an aspect of the present invention.

FIG. 6 illustrates a methodology 500 to facilitate laser capture microdissection imaging performance in accordance with the present invention. While, for purposes of simplicity of explanation, the methodology is shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

Proceeding to 510, lenses are selected having diffraction-limited characteristics at about the same size of a pixel in order to provide unit-mapping and optimization of the k-space design. At 514, lens characteristics are also selected to mitigate reduction of spatial frequencies within k-space. As described above, this generally implies that larger diameter optics are selected in order to mitigate attenuation of desired k-space frequencies of interest. At 518, a lens configuration is selected such that pixels, having a pitch "P", at the image plane defined by the position of a sensor are scaled according to the pitch to an object field of view at about the size of a diffraction-limited spot (e.g., unit-mapped) within the object field of view. At 522, an image is generated by outputting data from a sensor for real time monitoring and storing the data in memory for direct display to a computer display and/or subsequent local or remote image processing and/or analysis within the memory.

Figure 7:
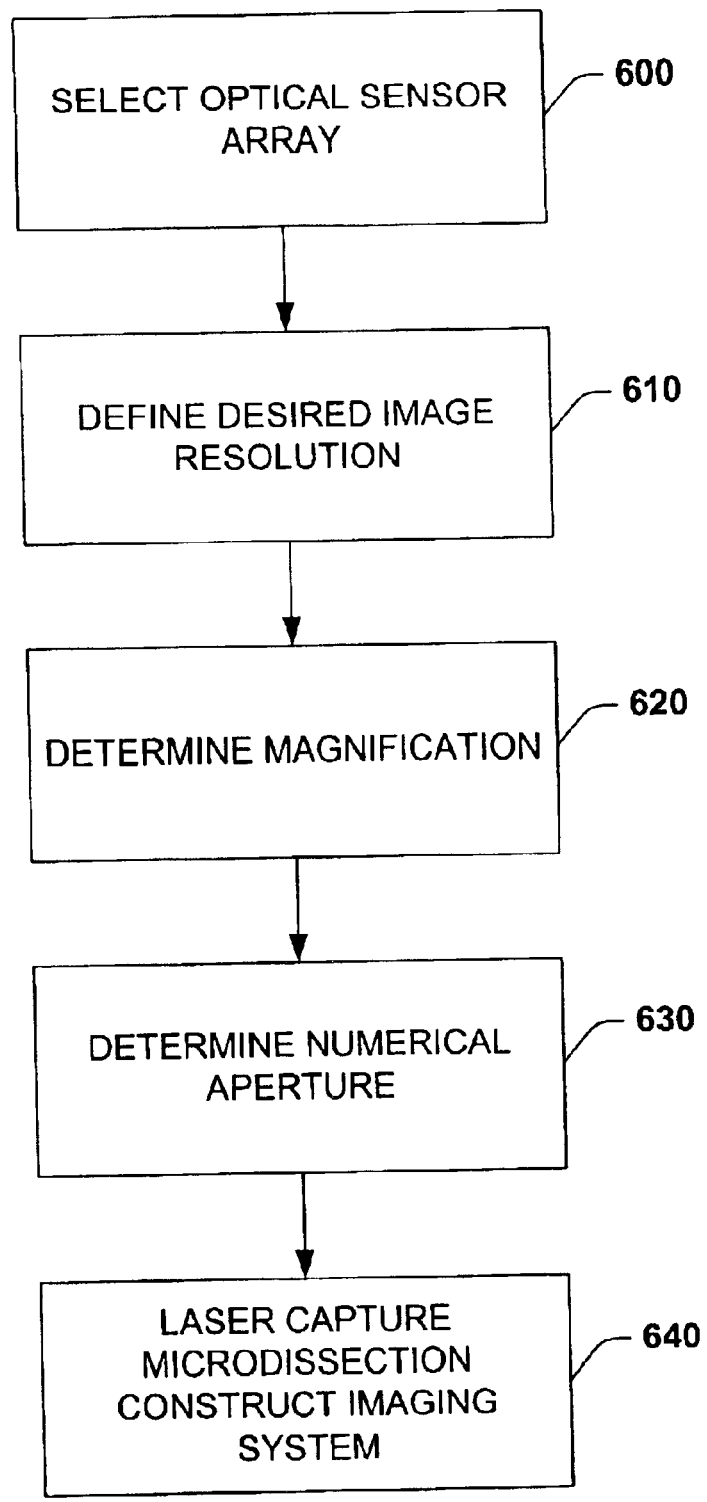
FIG. 7 is a flow diagram illustrating a laser capture microdissection imaging methodology in accordance with one aspect of the present invention.

FIG. 7 illustrates another methodology that can be employed to design a laser capture microdissection imaging system in accordance with an aspect of the present invention. The methodology begins at 600 in which an appropriate sensor array is chosen for the laser capture microdissection imaging system. The sensor array includes of a matrix of receptor pixels having a known pitch size, usually defined by the manufacturer. The sensor can be substantially any shape (e.g., rectangular, circular, square, triangular, and so forth). By way of illustration, assume that a simple sensor of 640×480 pixels having a pitch size of 10 $\mu$m is chosen. It is to be understood and appreciated that a laser capture microdissection imaging system can be designed for any type and/or size of sensor array in accordance with the present invention.

Next at 610, an image resolution is defined. The image resolution corresponds to the smallest desired resolvable spot size at the image plane. The image resolution can be defined based on the specific application(s) for which the laser capture microdissection imaging system is being designed, such as any resolution that is greater than or equal to a smallest diffraction limited size. Thus, it is to be appreciated that resolution becomes a selectable design parameter that can be tailored to provide desired image resolution for virtually any type of application. In contrast, most conventional laser capture microdissection imaging systems tend to limit resolution according to Rayleigh diffraction, which provides that intrinsic spatial resolution of the lenses cannot exceed limits of diffraction for a given wavelength.

After selecting a desired resolution (610), an appropriate amount of magnification is determined at 620 to achieve such resolution. For example, the magnification is functionally related to the pixel pitch of the sensor array and the smallest resolvable spot size. The magnification (M) can be expressed as follows:

$$M = x/y \qquad \text{Eq. 1}$$

where:

x is the pixel pitch of the sensor array; and y is the desired image resolution (minimum spot size).

So, for the above example where the pixel pitch is 10 $\mu$m and assuming a desired image resolution of 1 $\mu$m, Eq. 1 provides a laser capture microdissection imaging system of power ten. That is, the lens system is configured to back-project each 10 $\mu$m pixel to the object plane and reduce respective pixels to the resolvable spot size of 1 micron.

The methodology of FIG. 7 also includes a determination of a Numerical Aperture at 630. The Numerical Aperture (NA) is determined according to well established diffraction rules that relate NA of the objective lens to the minimum resolvable spot size determined at 610 for the laser capture microdissection imaging system. By way of example, the calculation of NA can be based on the following equation:

$$NA = \frac{0.5 \times \lambda}{y} \qquad \text{Eq. 2}$$

where:

$\lambda$ is the wavelength of light being used in the optical system; and y is the minimum spot size (e.g., determined at 610).

Continuing with the example in which the laser capture microdissection imaging system has a resolved spot size of y=1 micron, and assuming a wavelength of about 500 nm (e.g., green light), a NA=0.25 satisfies Eq. 2. It is noted that relatively inexpensive commercially available objectives of power 10 provide numerical apertures of 0.25.

It is to be understood and appreciated that the relationship between NA, wavelength and resolution represented by Eq. 2 can be expressed in different ways according to various factors that account for the behavior of objectives and condensers. Thus, the determination at 630, in accordance with an aspect of the present invention, is not limited to any particular equation but instead simply obeys known general physical laws in which NA is functionally related to the wavelength and resolution. After the lens parameters are designed according to the selected sensor (600), the corresponding optical components can be arranged to provide a laser capture microdissection imaging system (640) in accordance with an aspect of the present invention.

Assume, for purposes of illustration, that the example laser capture microdissection imaging system created according to the methodology of FIG. 7 is to be used for microscopy. By way of comparison, in classical microscopy, in order to image structures of a size approaching 1 micron (and below), magnifications of many hundreds usually are required. The basic reason for this is that such optics conventionally are designed for the situation when the sensor of choice is the human eye. In contrast, the methodology of FIG. 7 designs the laser capture microdissection imaging system around the sensor, which affords significant performance increases at reduced cost.

In the k-space design methodology, according to an aspect of the present invention, the laser capture microdissection imaging system is designed around a discrete sensor that has known fixed dimensions. As a result, the methodology provides a far more straight-forward optical system design approach to "back-project" the sensor size onto the object plane and calculate a magnification factor. A second part of the methodology helps ensure that the optics that provide the magnification have a sufficient NA to optically resolve a spot of the same dimensions as the back-projected pixel. Advantageously, a laser capture microdissection imaging system designed in accordance with an aspect of the present invention can utilize custom and/or off-the-shelf components. Thus, for this example, inexpensive optics can be employed in accordance with an aspect of the present invention to obtain excellent results, but well-corrected microscope optics are relatively cheap. If custom-designed optics are utilized, in accordance with an aspect of the present invention, then the range of permissible magnifications and numerical apertures becomes immense, and some performance gains can be realized over the use of off-the-shelf optical components.

Although any laser capture microdissection techniques may be combined with the imaging system described herein, several specific embodiments are described below to illustrate by example combinations of laser capture microdissection techniques and the imaging system described herein.

Figure 8:
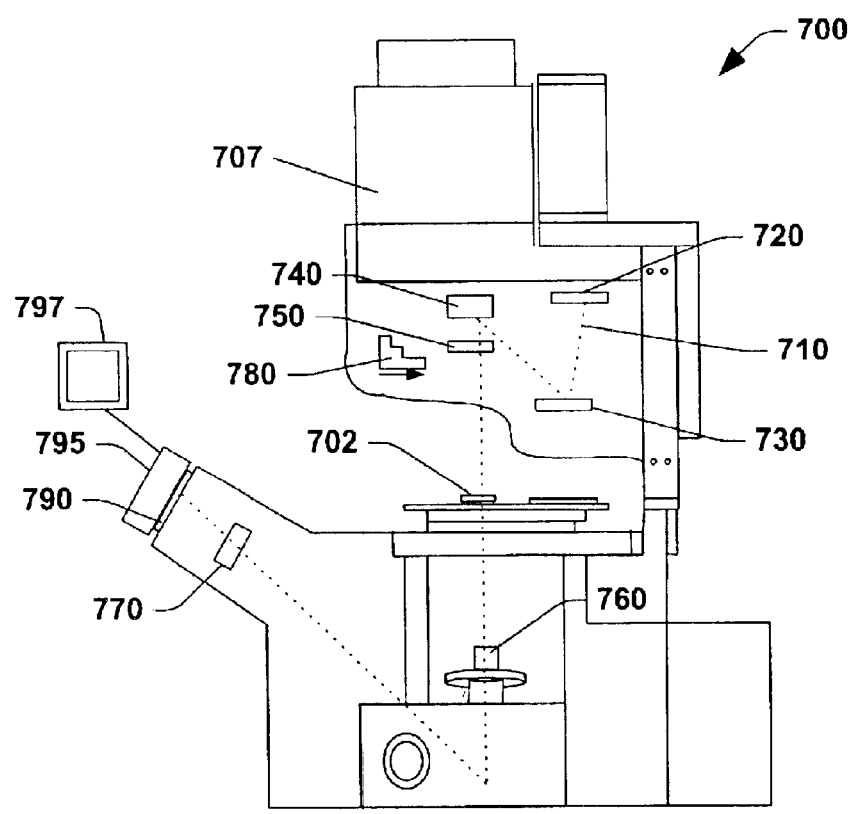
FIG. 8 is a partial cross-sectional view of a laser capture microdissection imaging system in accordance with one aspect of the present invention.

Referring to FIG. 8, a block schematic diagram of a laser capture microdissection imaging system 700 according to one aspect of the invention is shown. A laser beam path 710 begins at a film activation laser 720. The laser beam path 710 is reflected by a mirror 730 and a dichroic mirror 740. The laser beam path 710 is then focused by a lens 750. The lens 750 can optionally be associated with structure for changing the beam diameter such as, for example, a variable aperture.

The laser beam path 710 passes towards the microcentrifuge tube cap 702 containing the tissue sample. A laser capture microdissection transfer film is coupled to the bottom of the microcentrifuge tube cap 702. A glass slide upon which the sample to be microdissected is located and upon which the microcentrifuge tube cap 702 is placed, is located in the primary optical axis of the inverted laser capture microdissection imaging system.

The laser beam path 710 passes through an objective lens 760 and is then reflected. White light from the illuminator 707 passes downward toward the microcentrifuge tube cap 702 through a dichroic mirror 740 and a focusing lens 750. A dichroic mirror 740 may allow white light from the illuminator 707 to pass directly down through the focusing lens 750 toward the microcentrifuge tube cap 702. Thus, the laser path 710 and the white light illumination are superimposed. The focusing lens 750 also adjusts the beam spot size.

It can be appreciated from FIG. 8 that in this embodiment the illuminator 707 and the objective lens 760 are located on opposite sides of the dichroic mirror 740. A transfer lens or image forming lens 770 is positioned between the objective lens 760 and the sensor 795. A cut-off filter 790 is positioned in front of the sensor 795. The cut-off filter 790 can reflect and/or absorb the energy from the laser beam. The sensor 795 is connected with a display 797, optionally through a memory (not shown). The display 797 may comprise a video monitor, LCD, computer screen, and the like.

The position of the laser beam path 710 with respect to the portion of the tissue sample that is to be acquired by the microcentrifuge tube cap 702 can be seen by an operator via the sensor 795/display 797. In idle mode, the laser beam path 710 provides a visible low amplitude signal that can be detected via the sensor 795/display 797. In pulse mode, the laser beam path 710 delivers energy to the microcentrifuge tube cap 702 and the optical characteristics of the cut-off filter 790 attenuate the laser beam path 710 sufficiently so that substantially none of the energy from the laser beam reaches the sensor 795.

Suitable laser pulse widths are about 0 seconds or more and about 1 second or less, such as about 50 milliseconds. The wavelength of the laser may be 810 nm. The spot size of the laser at the EVA material located on microcentrifuge tube cap 702 is variable from 0.25 µm to 250 µm, such as about 20 µm. The laser can be connected to the rest of the optical subsystem with a fiber optical coupling. Smaller spot sizes are obtainable using suitable devices such as diffraction limited laser diodes and/or single mode fiber optics. Single mode fiber allows a diffraction limited beam.

While the laser diode can be run in a standard mode such as $TEM_{00}$, other intensity profiles can be used for different types of applications. Further, the beam diameter could be changed with a stepped lens instead of lens 750. For example, inserting a stepped glass prism 780 into the beam so the beam strikes one step tread changes the optical path length and alters the spot size.

Figure 9:
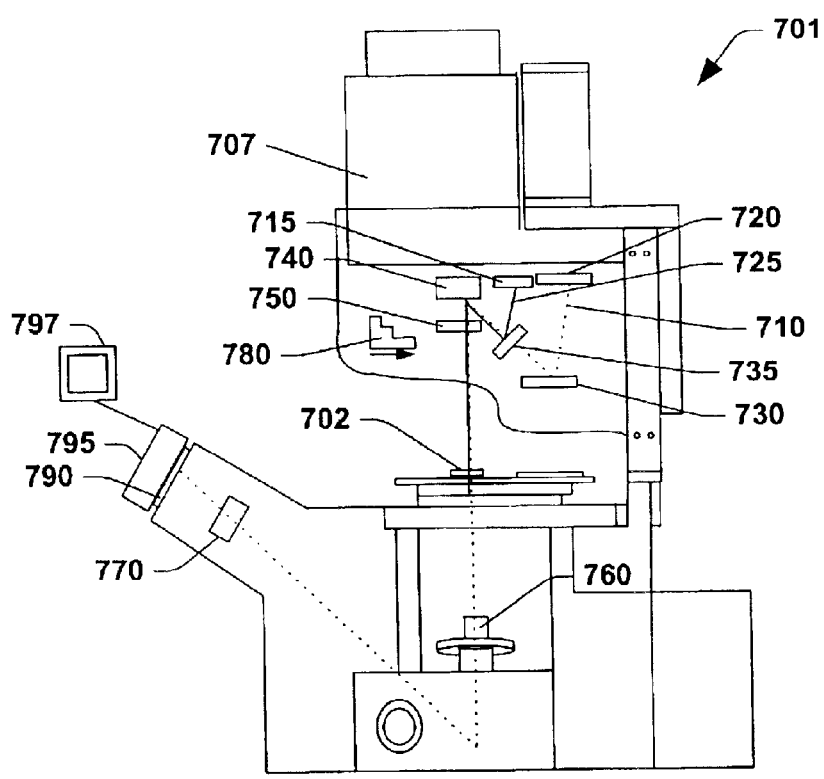
FIG. 9 is a partial cross-sectional view of a laser capture microdissection imaging system in accordance with one aspect of the present invention.

Turning now to FIG. 9, a schematic block diagram of another embodiment of a laser capture microdissection imaging system 701 according to another aspect of the present invention is shown (similar to the system of FIG. 8, and features in common have the same reference numeral but may not be discussed). In this embodiment, a light source 715 (e.g., diode laser or other suitable excitation source), emits a specific wavelength or wavelength range. The specific wavelength or wavelength range of a beam 725 emitted by the light source 715 is selected, or filtered, to excite a fluorescent system (such as chemical markers and optical filtering techniques that are known in the industry) that is incorporated in or applied to the tissue sample for microdissection. The frequency of a beam 725 emitted by the excitation source 715 can be tuned as needed. The tissue sample includes at least one of chromophores and fluorescent dyes (synthetic or organic), and, the process of operating the laser capture microdissection imaging system includes identifying at least a portion of the tissue sample with light that excites the at least one member, before transferring that portion of the tissue sample to the laser capture microdissection transfer film.

Still referring to FIG. 9, the beam 725 is reflected by a mirror 735. The beam 725 is then reflected by the dichroic mirror 740. In this way the beam 725 can be made coincident with both the laser beam path 710 and the illuminating light, such as white light, UV light, and the like, from illuminator 707. It is noted that the beam 725 and the laser beam path 710 are shown in a spaced-apart configuration for clarity only. The beam 725 and the laser beam path 710 can be coaxial. Fluorescence emitted by the tissue sample beneath the microcentrifuge tube cap 702 then travels through the objective lens 760, the transfer lens 770, captured by the sensor 795, and viewed by the display 797.

Further, the beam diameter could be changed with a stepped lens instead of lens 750. For example, inserting a stepped glass prism 780 into the beam so the beam strikes one step tread changes the optical path length and alters the spot size. A cut-off filter 790 is positioned in front of the sensor 795.

Figure 10:
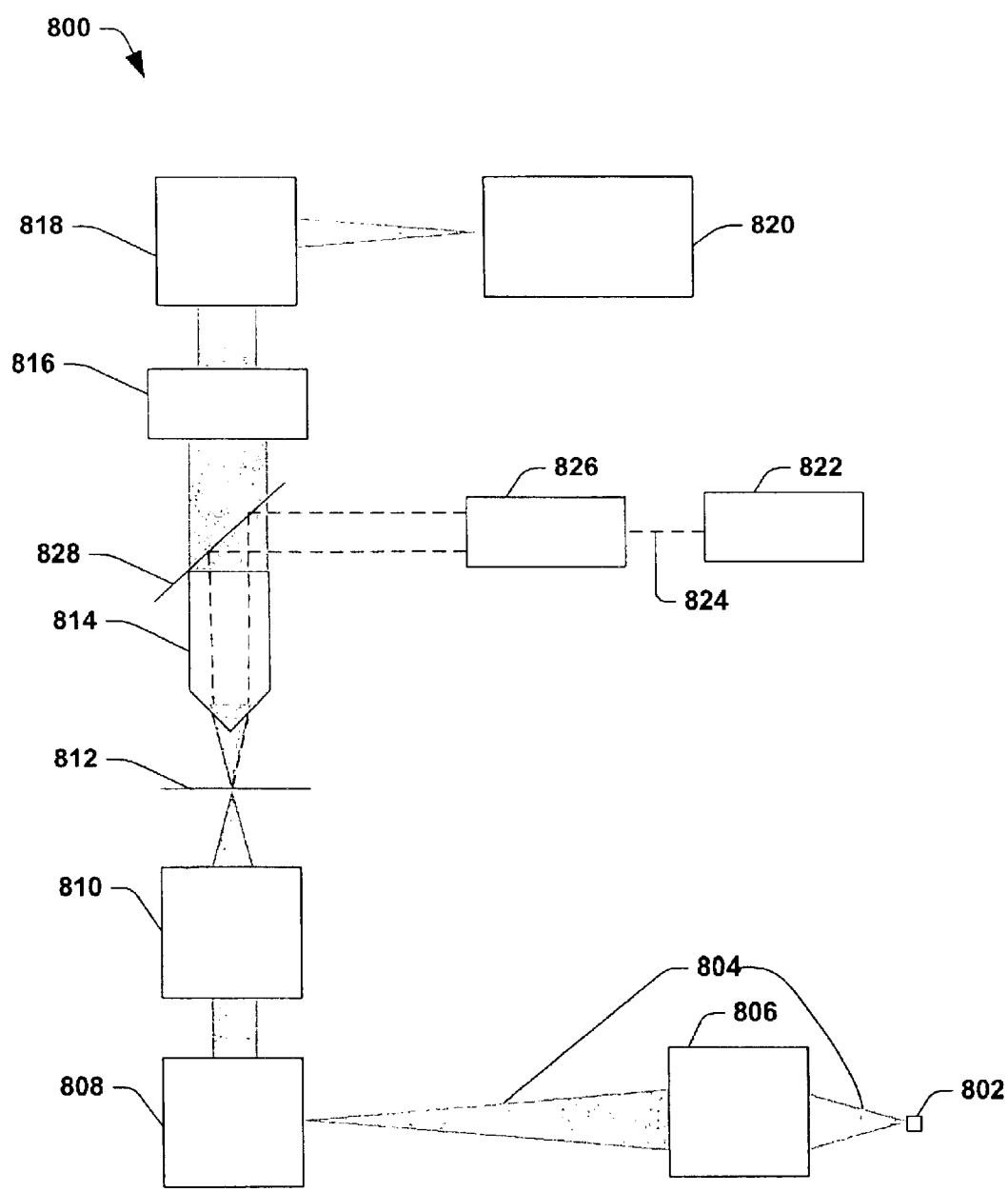
FIG. 10 is a high level schematic diagram of a laser capture microdissection imaging system in accordance with one aspect of the present invention.

Referring to FIG. 10, a high level schematic block diagram is provided to exemplify another embodiment of a laser capture microdissection imaging system 800 according to another aspect of the present invention. An illuminator 802 provides illuminating light 804 which travels to and through the object plane and eventually to the sensor/camera 820. Specifically, the light travels through a condenser 806, is reflected by fold mirror 808 towards the object plane, through microscope condenser 810 where it is focused to the object plane 812 that contains the laser capture microdissection sample (not shown), through an objective lens 814 and laser mirror 828 after which it is focused by a transfer lens or an image forming lens 816, and fold mirror 818 directs the light to the sensor/camera 820.

Laser 822 generates a laser beam 824 of suitable wavelength which may travel through optional expander/collimator 826 before being reflected by laser mirror 828 towards the object plane 812. The laser may be expanded using a telescope to utilize the physical space allowed for the Fourier components of the beam. The expander/collimator 826 can be adjustable thereby providing a slightly diverging/converging beam in order to change the projected spot size at the object plane.

The laser mirror 812 makes the laser beam 824 and optical axes or illuminating light 804 collinear. Preferably the laser mirror 812 is a narrowband mirror with a reflectivity at the laser wavelength only, and transparent at viewing or other visible wavelengths. In this embodiment, the laser beam 824 may be introduced into the optical path via the infinity space. The laser mirror 812 can be mounted on servos/adjusters to give a small degree of rotation in two axes, which facilitates precisely positioning the projected laser spot in the optical field of view.

The objective lens 814 is preferably transparent at viewing wavelengths and the laser wavelength. In this and other embodiments, the laser beam 824 can be almost any wavelength, as the laser mirror 828 ensures that the laser beam 824 is not substantially "seen" or detected by the viewing path at the sensor/camera 820.

In another embodiment, a second, visible laser beam (such as a 630 nm diode) may be projected with laser beam 824 and mixed therewith so that a projected spot can be viewed on the object scene and used as a visible indicator of the location where the laser energy is deposited, and the diameter of the laser beam 824 spot is viewed as an overlay on the viewed image.

Generally the benefits of the embodiment of FIG. 10 include one or more of the k-space design low magnification and large working distance; the amount of laser optics is minimized; flexibility in laser spot positioning and sizing; changing the microscope objective changes the laser spot size simultaneously, thus the image and laser are matched in k-space components; with the inverted microscope design, it is not necessary to look through the sample; and automated computer control to identify cells of interest, with computer driven servo adjustments to position laser can be optionally provided.

Several additional advantages are available with the laser capture microdissection imaging system when certain optional modifications are implemented. For example, when the microscope objective is employed as both the viewing imager and laser projector, matching in k-space the minimum resolvable spot sizes for the laser and the viewer is promoted. When the laser beam is steerable (and viewable), the problems of alignment between the optical paths are minimized. By making the laser collimator adjustable, variable spot sizes can easily be projected onto the object plane. Additionally, in the case of an IR laser, the laser mirror can be made slightly "leaky" to use the inherent IR sensitivity of a semiconductor sensor to directly view the projected laser beam spot at the object plane. In this connection, it is preferable to operate the laser at low power CW to view the positioning of the spot, and then pulse the laser to melt the plastic film.

In accordance with the concepts described above in relation to FIGS. 1–10, a plurality of related laser capture microdissection imaging applications and methods can be enabled and enhanced by the present invention. For example, these applications can include but are not limited to imaging, control, inspection, microscopy and/or other analysis.

The laser capture microdissection imaging system of the present invention enables computer driven control or automated process control to obtain cell samples from tissue samples. In this connection, a computer or processor, coupled with the laser capture microdissection imaging system, contains or is coupled to a memory or data base containing images of diseased cells of various types. The laser capture microdissection imaging system secures images of many cells within a given tissue sample from which a cell sample is to be taken, and the images of the cells are compared with images of diseased cells in the memory.

If the computer/processor determines that a sufficient degree of similarity is present between particular cells in a tissue sample and saved images of diseased cells, then the laser beam is activated and directed at the particular cells of interest to obtain a cell sample from the tissue sample by laser capture microdissection. If the computer/processor determines that a sufficient degree of similarity is not present between particular cells in a tissue sample and saved images of diseased cells, then the tissue sample is repositioned and additional images are compared with images of diseased cells in the memory. It is to be appreciated that statistical methods can be applied by the computer/processor to assist in the determination that a sufficient degree of similarity is present between particular cells in a tissue sample and saved images of diseased cells. Any suitable correlation means or software/hardware may be employed by the computer/processor.

The computer/processor may be coupled to a controller which controls a servo motor or other means of moving the tissue sample within the object plane so that the laser beam is directed at diseased cells. That is, motors, adjusters, or other mechanical means can be employed to move the tissue sample slide relative to the target spot of the laser beam in the object field of view.

Moreover, since the images of the laser capture microdissection process are optimized for viewing from a computer screen, television, or closed circuit monitor, remote and web based viewing and control may be implemented. Real time imaging facilitates securing cell samples from a particular location of a tissue sample in a quick and efficient manner.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A laser capture microdissection system, comprising:
   a laser and laser delivering system for directing a laser beam at a tissue sample; and
   an imaging system for imaging a portion of the tissue sample at which the laser beam is directed, the imaging system comprising:
   a sensor having one or more receptors; and
   an image transfer medium to scale the one or more receptors to have a size in an object field of view that is about the size of a diffraction limited spot in the object field of view.

2. The laser capture microdissection system of claim 1, wherein the receptors comprise pixels, the image transfer medium scales projected pixel size to the diffraction limited spot in the object field of view, and the projected pixel size and the diffraction limited spot are within 20% of each other.

3. The laser capture microdissection system of claim 1, wherein the receptors comprise pixels, the image transfer medium scales projected pixel size and the diffraction limited spot in the object field of view, and the projected pixel size and the diffraction limited spot are within 5% of each other.

4. The laser capture microdissection system of claim 1, the image transfer medium further comprising at least one of an aspherical lens, a multiple lens configuration, a fiber optic taper, an image conduit, and a holographic optic element.

5. The laser capture microdissection system of claim 4, the multiple lens configuration further comprising a first lens positioned toward the object field of view and a second lens positioned toward the sensor, the first lens sized to have a focal length smaller than the second lens to provide an apparent reduction of the one or more receptors within the object field of view.

6. The laser capture microdissection system of claim 1, the sensor further comprising at least one of digital sensor, analog sensor, Charge Coupled Device sensor, CMOS sensor, Charge Injection Device sensor, an array sensor, and a linear scan sensor.

7. The laser capture microdissection system of claim 1, further comprising a computer and a memory to receive an output from the one or more sensors, the computer storing the output in the memory.

8. The laser capture microdissection system of claim 7, the computer mapping the memory to a display to enable manual analysis of an image.

9. The laser capture microdissection system of claim 8, the image having a depth of field of about 1 or more microns and about 50 microns or less at an Effective Resolved Magnification of about 750 times or more and about 5000 times or less.

10. The laser capture microdissection system of claim 8, the image having an effective resolved magnification of about 2500 times or more and about 5000 times or less, the image providing a spatial field of view of about 0.250 millimeters or less.

11. The laser capture microdissection system of claim 1, the image transfer medium enabling a working distance from an object plane to the image transfer medium of about 0.1 millimeters or more and about 20 millimeters or less.

12. The laser capture microdissection system of claim 1, the sensor comprises pixels, and the image transfer medium unit mapps projected pixels in the object field of view to the diffraction limited spot in the object field of view.

13. The laser capture microdissection system of claim 1, further comprising an illumination source to illuminate one or more non-luminous objects within the object field of view.

14. The laser capture microdissection system of claim 13, the illumination source comprises at least one of wavelength-specific lighting, broad-band lighting, continuous lighting, strobed lighting, Kohler illumination, Abbe illumination, phase-contrast illumination, darkfield illumination, brightfield illumination and Epi illumination.

15. The laser capture microdissection system of claim 13, the illumination source further comprising at least one of coherent light, non-coherent light, visible light and non-visible light, the non-visible light being suitably matched to a sensor adapted for non-visible light.

16. A laser capture microdissection method, comprising:
   placing a transfer film over a tissue sample;
   positioning the transfer film covered tissue sample within an object plane of an imaging system for imaging a portion of the transfer film covered tissue sample, the imaging system comprising:
   a sensor having one or more receptors; and
   an image transfer medium to scale the one or more receptors to have a size in an object field of view that is about the size of a diffraction limited spot in the object field of view;
   contacting the transfer film covered tissue sample with a laser beam whereby a portion of the tissue sample adheres to the transfer film;
   removing the transfer film and the portion of the tissue sample adhering to the transfer film from a remaining portion of the tissue sample.

17. The method of claim 16, the imaging system further comprising a computer display for viewing an image.

18. The method of claim 16, wherein the imaging system produces an image by:

determining a pitch size between adjacent pixels on the sensor;

determining a resolvable object size in the object field of view; and scaling the pitch size through an optical medium to correspond with the resolvable object size.

19. A laser capture microdissection system, comprising:

a laser and laser delivering system for directing a laser beam at a tissue sample;

an imaging system for imaging a portion of the tissue sample at which the laser beam is directed, the imaging system comprising:
- a sensor having one or more receptors; and
  - an image transfer medium to scale the one or more receptors to have a size in an object field of view that is about the size of a diffraction limited spot in the object field of view;

a memory comprising stored image data; and a processor for comparing an image generated by imaging system to stored image data, the processor coupled to the memory and the imaging system.

20. The laser capture microdissection system of claim 19, further comprising a controller coupled to the processor and the imaging system capable of positioning the tissue sample relative to the laser beam based on a signal from the processor.

* * * * *